United States Patent
Litwak

(10) Patent No.: US 10,595,879 B1
(45) Date of Patent: Mar. 24, 2020

(54) BLADE FOR OSTEOTOME

(71) Applicant: Ostech Medical, Inc., Keyport, NJ (US)

(72) Inventor: Alfred Anthony Litwak, Keyport, NJ (US)

(73) Assignee: Palix Medical LLC, Keyport, NJ (US)

( * ) Notice: Subject to any disclaimer, the term of this patent is extended or adjusted under 35 U.S.C. 154(b) by 496 days.

(21) Appl. No.: 15/369,839

(22) Filed: Dec. 5, 2016

(51) Int. Cl.
*A61B 17/14* (2006.01)

(52) U.S. Cl.
CPC .................... *A61B 17/142* (2016.11)

(58) Field of Classification Search
CPC ... A61B 17/16; A61B 17/1604; A61B 17/162; A61B 17/1626; A61B 17/1628; A61B 17/1633; A61B 17/1635; A61B 17/164; A61B 17/1642; A61B 17/1655; A61B 17/1657; A61B 17/1659; A61B 17/1662–1693; A61B 17/1695
USPC ........................................................ 606/84
See application file for complete search history.

(56) References Cited

U.S. PATENT DOCUMENTS

| | | | |
|---|---|---|---|
| 2,550,347 A | 4/1951 | Gruber | |
| 4,036,236 A | 7/1977 | Rhodes, Jr. | |
| 4,150,675 A * | 4/1979 | Comparetto | A61B 17/1604 30/302 |
| 4,584,999 A | 4/1986 | Arnegger | |
| 4,600,005 A * | 7/1986 | Hendel | B26D 3/06 30/167 |
| 4,617,930 A | 10/1986 | Saunders | |
| 4,768,504 A | 9/1988 | Ender | |
| 5,095,875 A | 3/1992 | Morris et al. | |
| 5,147,364 A * | 9/1992 | Comparetto | A61B 17/15 606/82 |
| 5,178,626 A | 1/1993 | Pappas | |
| D342,313 S * | 12/1993 | Hood | D24/133 |
| D344,801 S * | 3/1994 | Hughes | D24/144 |
| 5,507,763 A | 4/1996 | Petersen et al. | |
| 5,676,680 A | 10/1997 | Lim | |
| 5,735,855 A * | 4/1998 | Bradley | A61B 17/151 606/79 |
| 6,110,175 A * | 8/2000 | Scholl | A61B 17/1604 606/79 |
| 6,187,012 B1 * | 2/2001 | Masini | A61B 17/15 606/99 |
| 6,485,495 B1 * | 11/2002 | Jenkinson | A61B 17/1604 606/167 |

(Continued)

*Primary Examiner* — Eric S Gibson
(74) *Attorney, Agent, or Firm* — Peter Materna

(57) ABSTRACT

A blade for use in an osteotome or other cutting device. The blade may have, in sequence, a cutting portion, a transition portion, and a gripping portion, with the transition portion being located between the cutting portion and the gripping portion. The cutting portion may be planar and have at least one cutting edge. The gripping portion may be non-planar. The transition portion may be smoothly contoured. The non-planar nature of the gripping portion may provide increased rigidity of the blade. All of the blade may have uniform thickness of material. Also provided may be a chuck for gripping the blade. The chuck may have an upper nest and a lower nest that in combination closely fit around the gripping portion. The chuck may have a movable pin that locks the gripping portion into the chuck. A portion of the chuck may be spring-loaded.

20 Claims, 10 Drawing Sheets

(56) References Cited

U.S. PATENT DOCUMENTS

| | | | |
|---|---|---|---|
| 6,790,211 B1* | 9/2004 | McPherson | A61B 17/8847 606/84 |
| 6,896,679 B2 | 5/2005 | Danger et al. | |
| 7,833,241 B2 | 11/2010 | Gant | |
| 8,328,813 B2 | 12/2012 | Raus | |
| 8,372,077 B2* | 2/2013 | Taylor | A61B 17/1637 606/82 |
| 8,545,501 B2* | 10/2013 | Wong | A61F 2/4644 606/79 |
| 8,672,943 B2 | 3/2014 | Fisher et al. | |
| 8,734,450 B2* | 5/2014 | Landon | A61B 17/142 30/337 |
| 8,852,221 B2 | 10/2014 | Boykin et al. | |
| 8,858,559 B2* | 10/2014 | Milburn | A61B 17/142 30/392 |
| 8,888,783 B2* | 11/2014 | Young | A61B 17/16 606/82 |
| 8,920,424 B2* | 12/2014 | Boykin | A61C 3/12 606/82 |
| 8,966,772 B2 | 3/2015 | Legrand et al. | |
| 9,198,776 B2* | 12/2015 | Young | A61F 2/4607 |
| 9,242,361 B2 | 1/2016 | Kaye, Jr. et al. | |
| 9,848,900 B2* | 12/2017 | Witt | A61B 17/320068 |
| 9,867,628 B2* | 1/2018 | Macke | A61B 17/1742 |
| 2004/0098000 A1* | 5/2004 | Kleinwaechter | B23D 61/006 D24/146 |
| 2007/0123893 A1* | 5/2007 | O' Donoghue | A61B 17/142 606/82 |
| 2010/0057118 A1 | 3/2010 | Dietz et al. | |
| 2011/0034932 A1* | 2/2011 | Paulos | A61B 17/16 606/84 |
| 2011/0288555 A1* | 11/2011 | Szanto | A61B 17/1637 606/84 |
| 2012/0144971 A1 | 6/2012 | Bohne | |
| 2014/0090537 A1 | 4/2014 | Campbell et al. | |
| 2014/0163558 A1 | 6/2014 | Cosgrove et al. | |
| 2014/0316415 A1* | 10/2014 | Young | A61B 17/16 606/84 |

* cited by examiner

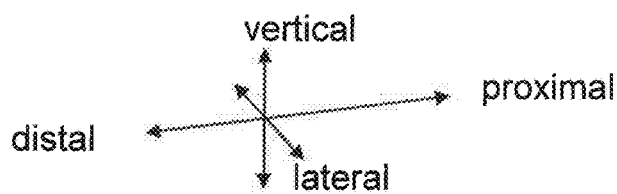
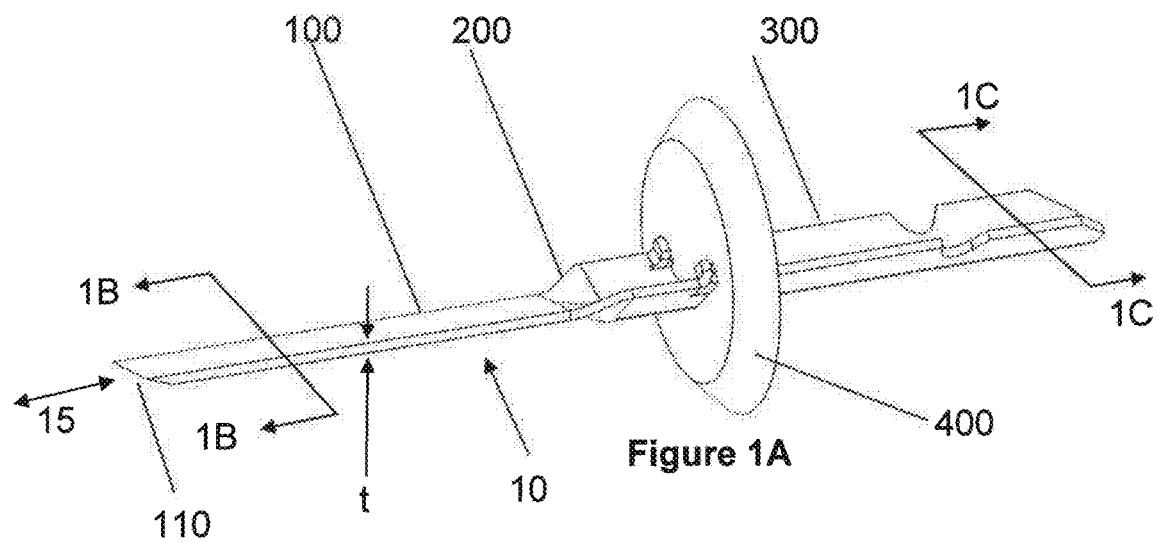
Figure 1A
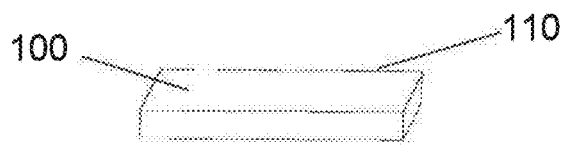
Figure 1B
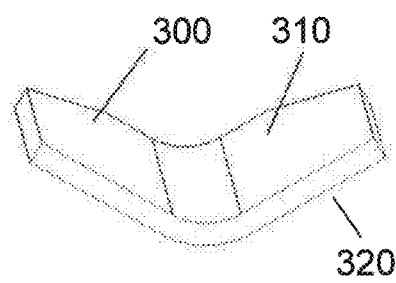
Figure 1C

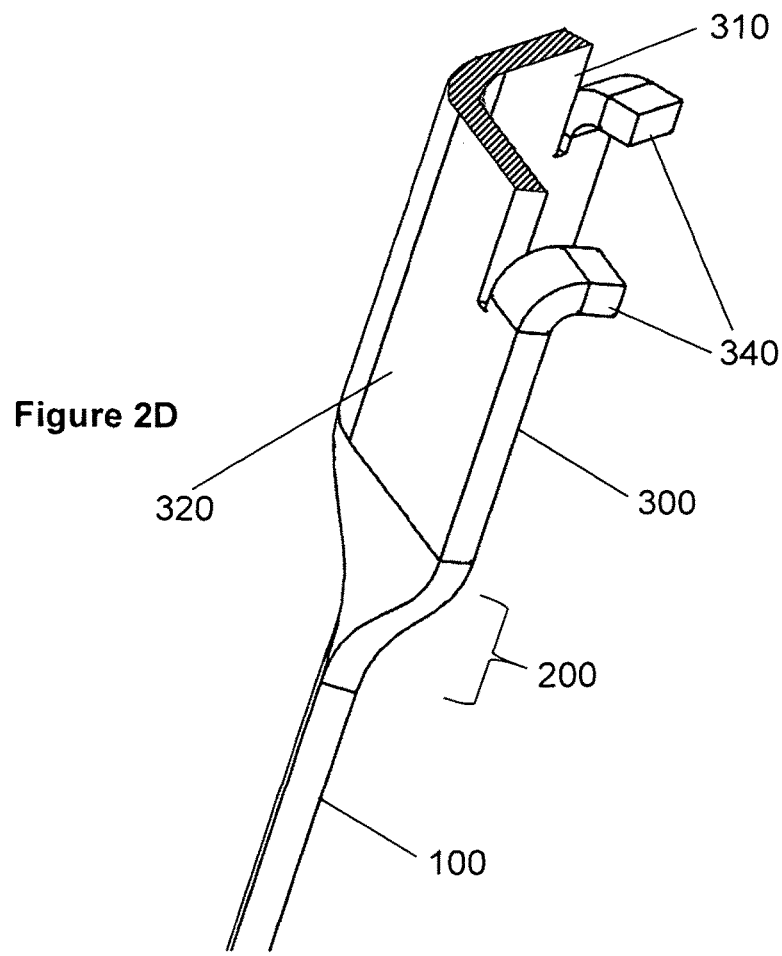
Figure 2D
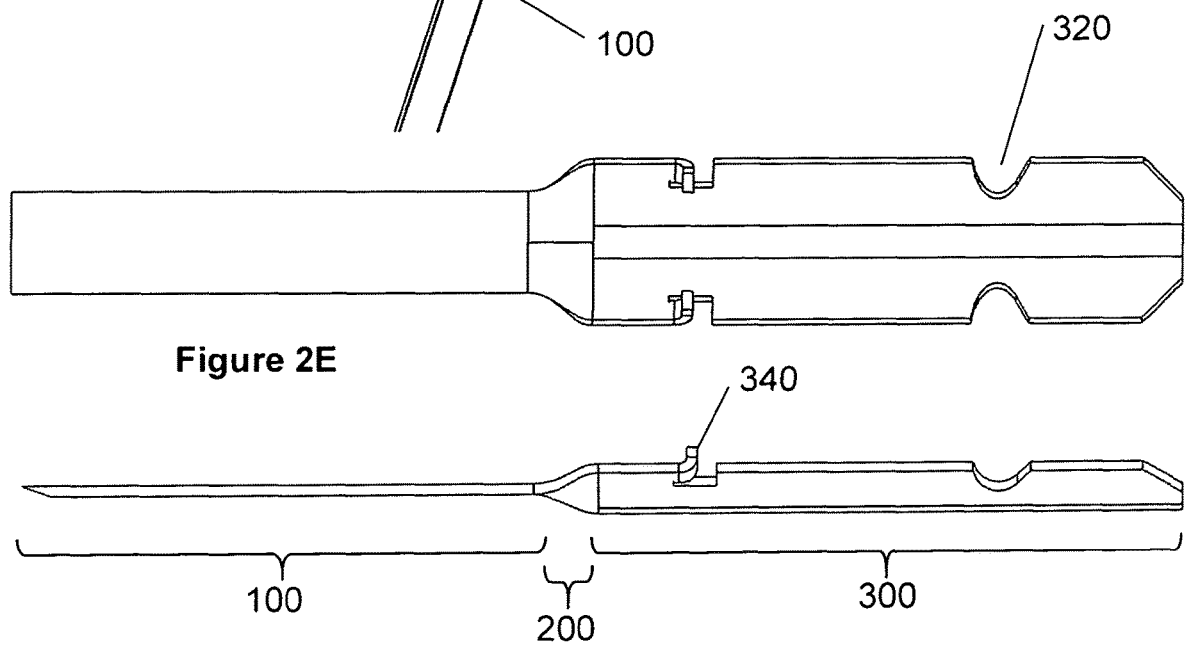
Figure 2E
Figure 2F

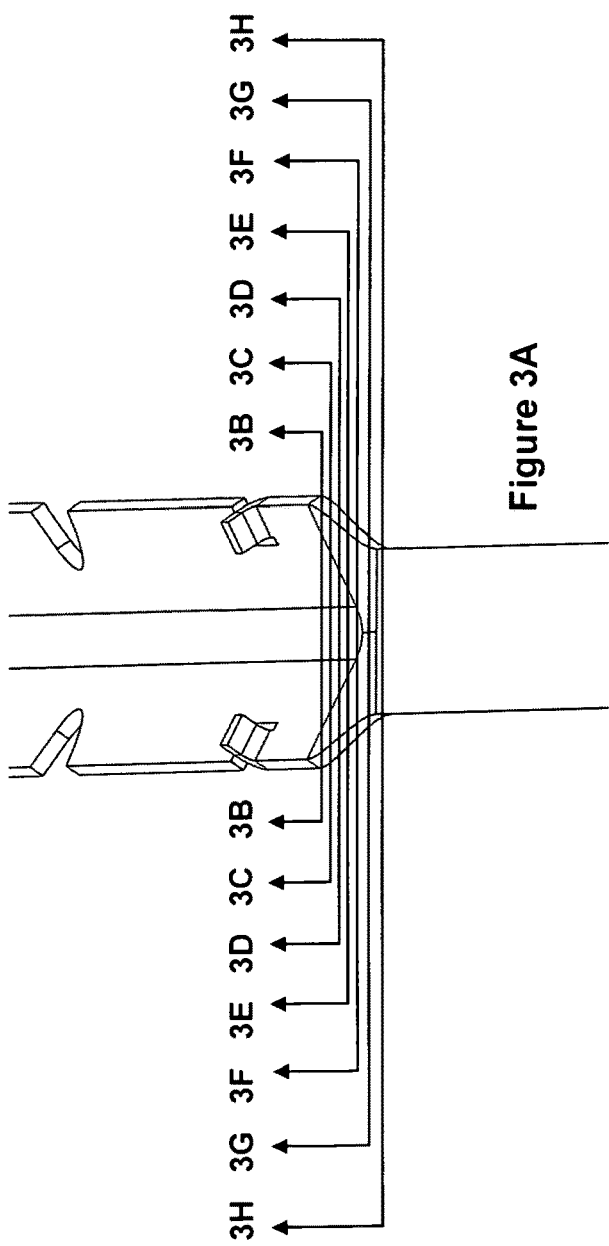
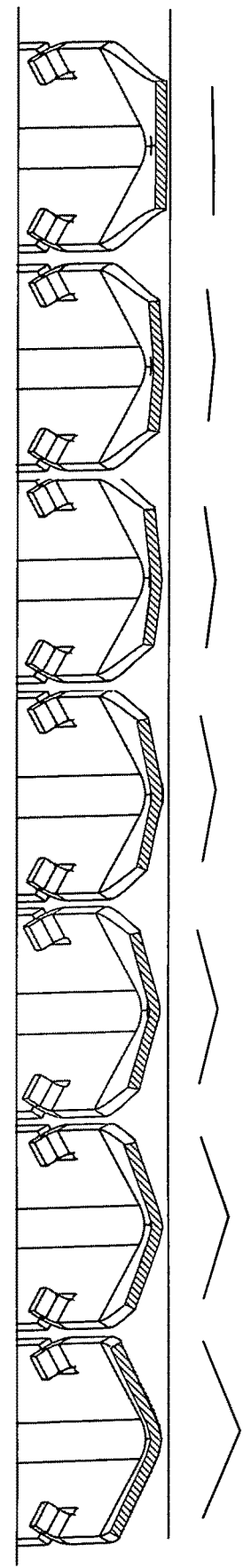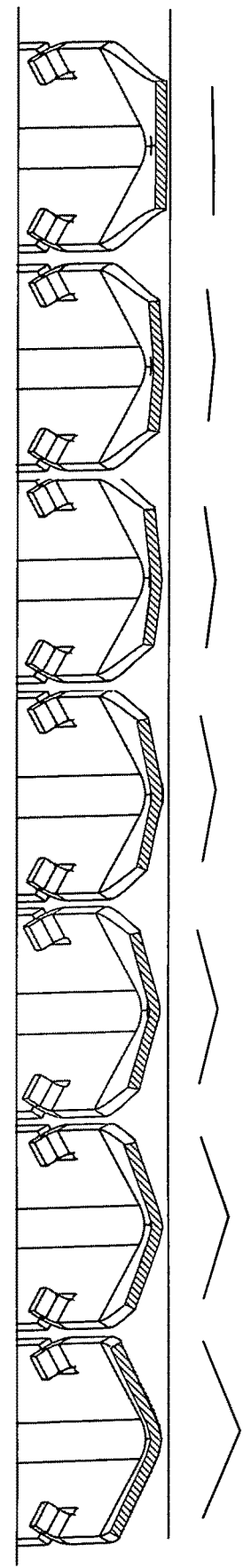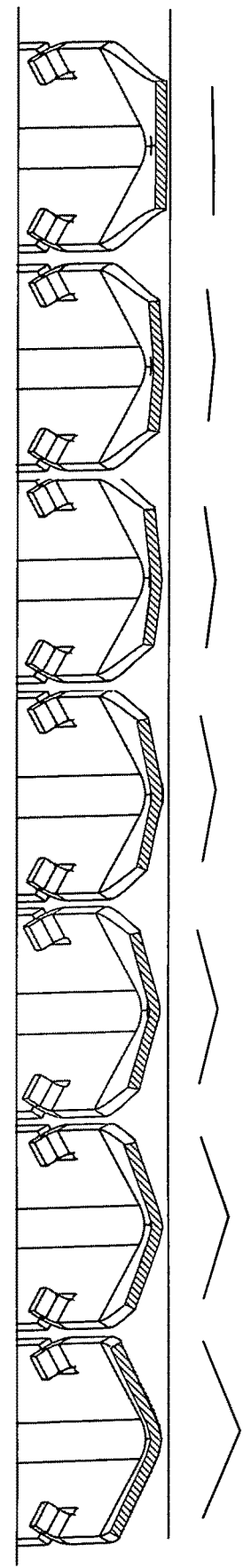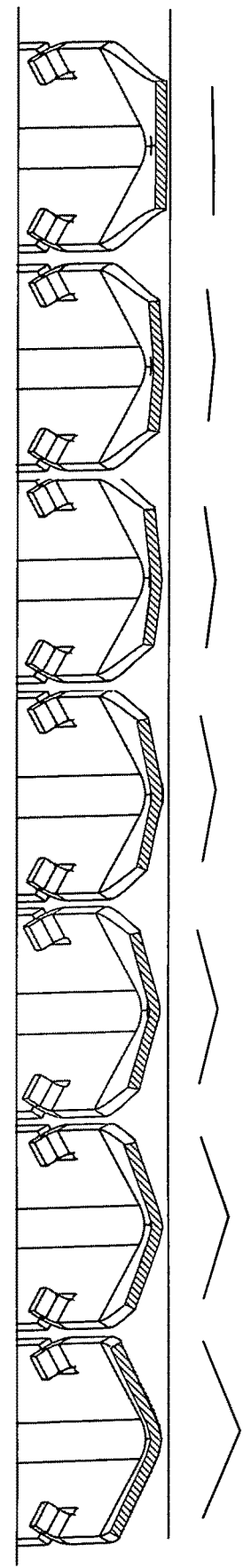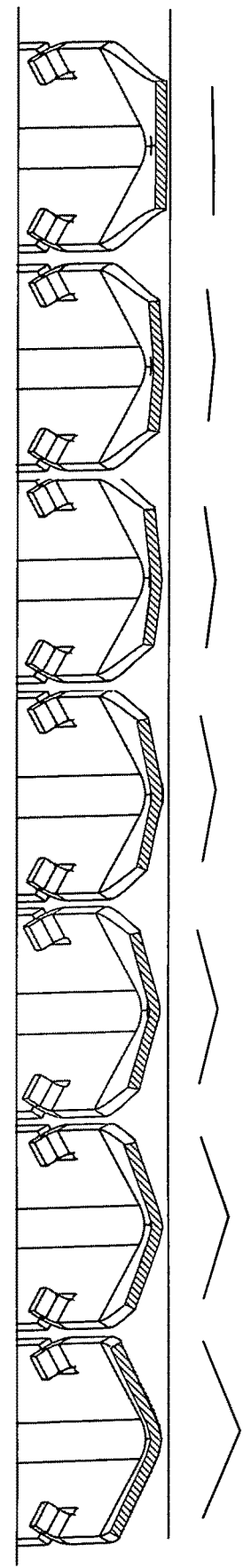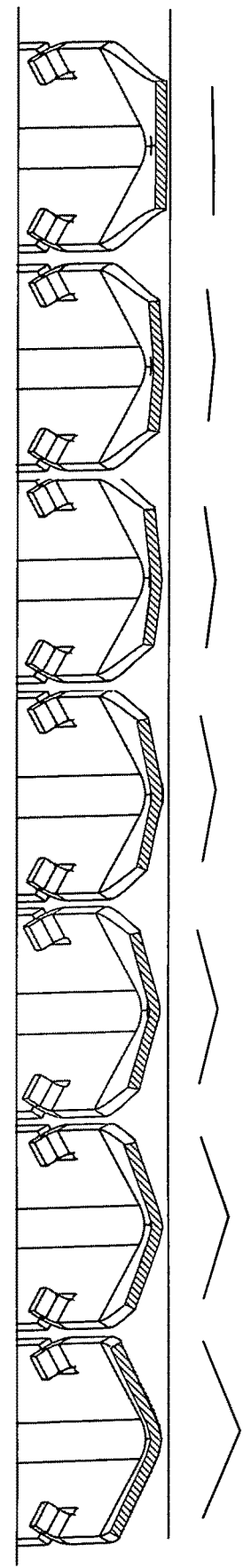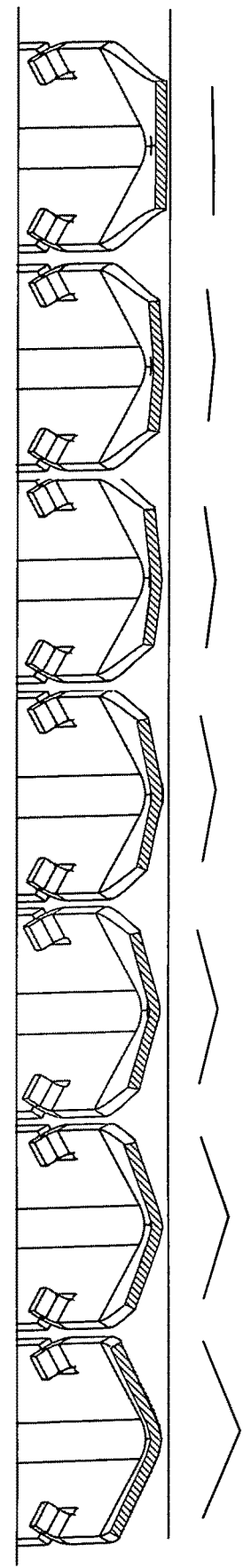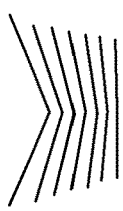

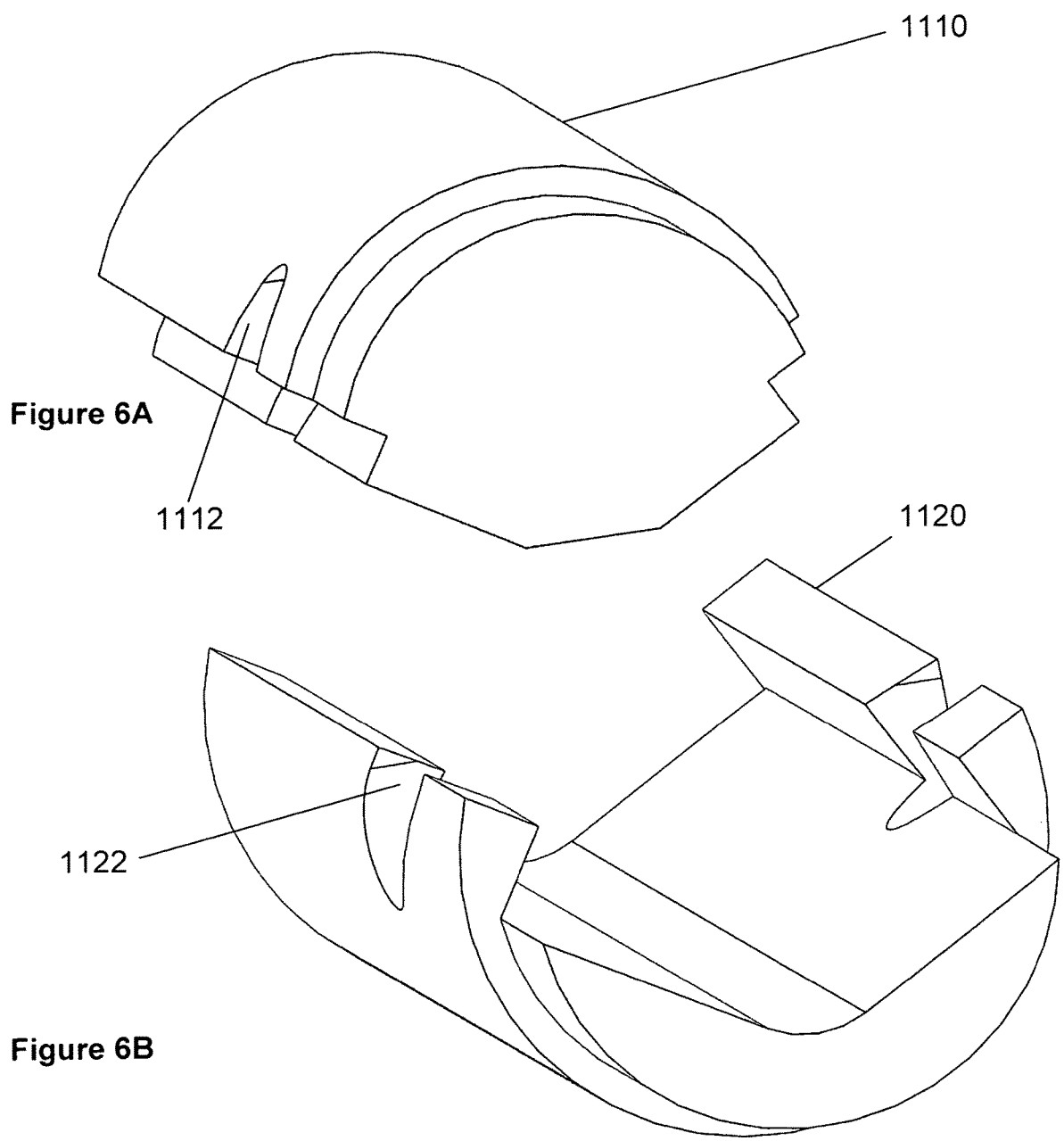

1800  1380  100

BLADE FOR OSTEOTOME

FIELD OF THE INVENTION

Embodiments of the invention pertain to cutting tools and orthopedic surgery.

BACKGROUND OF THE INVENTION

Orthopedic surgery frequently requires the use of tools and blades to cut bone. Such tools may be pneumatically powered, electric powered, or hand operated. Although a variety of such tools and blades exist, there still remains need for improvement as far as surgeon convenience, ease of access to a surgical site, and geometric properties of the blade.

SUMMARY OF THE INVENTION

In embodiments of the invention, there may be provided a blade for use in cutting, the blade comprising: a cutting portion; a transition portion that is continuous with the cutting portion; and a gripping portion that is continuous with the transition portion, wherein the blade has a longitudinal axis, wherein the cutting portion is planar and has at least one cutting edge that is adapted for cutting, wherein the gripping portion is non-planar, and wherein the transition portion has a three-dimensional surface transitioning between the cutting portion and the gripping portion. There may also be provide a chuck that is suitable to grip, capture or retain the gripping portion of the blade.

BRIEF DESCRIPTION OF THE ILLUSTRATIONS

Embodiments of the invention are further described but are in no way limited by the following illustrations.

FIG. 1A shows a three-dimensional perspective view of a blade of an embodiment of the invention.

FIG. 1B is a sectional view of the cutting portion of the blade of FIG. 1A.

FIG. 1C is a sectional view of the gripping portion of the blade of FIG. 1A.

FIG. 2D is a perspective view of a portion of the blade showing the transition portion, with the view being from the side but also showing some perspective. Again, in this illustration, some of the blade is cut off for clarity of illustration.

FIG. 2E is a top view of the blade.

FIG. 2F is a side view of the blade.

FIG. 3A is three-dimensional view of the blade from above at an angle, illustrating various sections of the transition portion.

FIGS. 3B-3H show various sections of FIG. 3A.

FIG. 3I shows a compilation of shapes from FIGS. 3B-3H.

FIG. 6A is a three-dimensional perspective view of the upper nest.

FIG. 6B is a three-dimensional perspective view of the lower nest.

DETAILED DESCRIPTION OF THE INVENTION

Figure 2A:
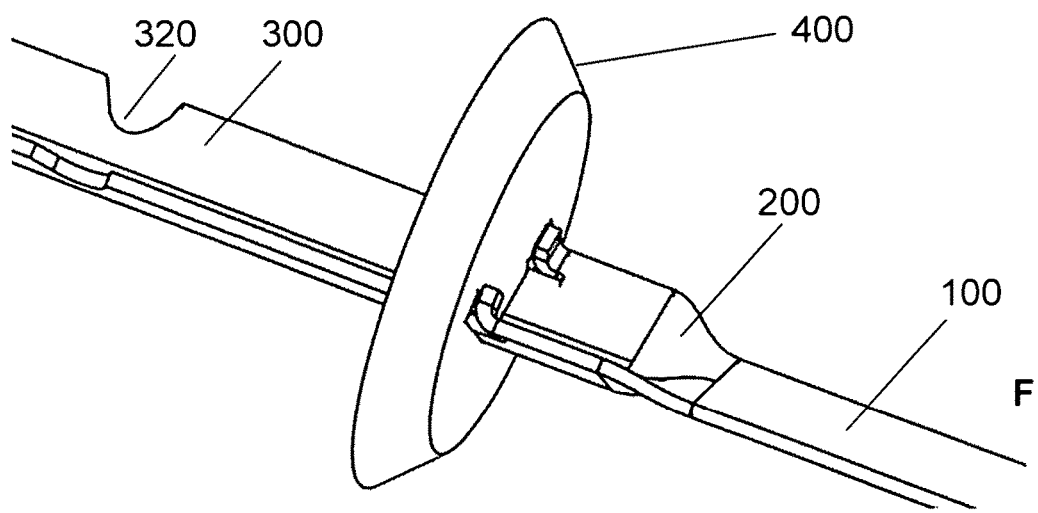
FIG. 2A is a three-dimensional perspective view of the blade, showing the cutting portion and the transition portion and the gripping portion, and also the splash guard.
Figure 2B:
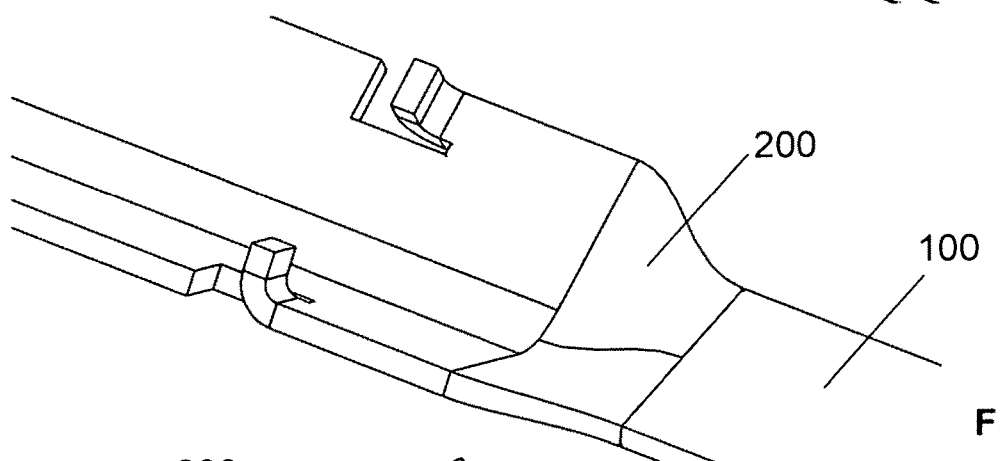
FIG. 2B is similar to FIG. 2A, but closer-up and with the splash guard omitted.
Figure 2C:
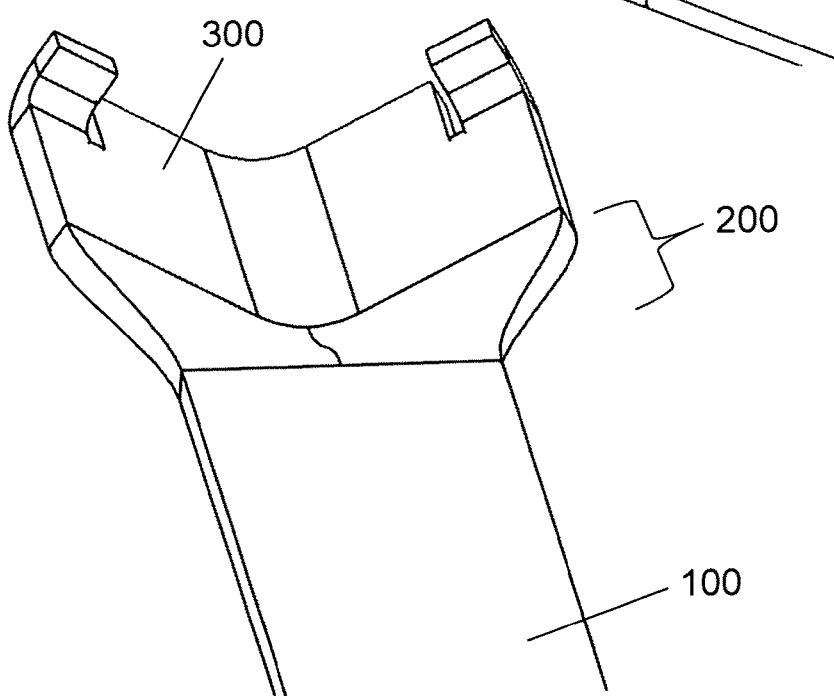
FIG. 2C is a three-dimensional perspective view of a portion of the blade, showing the transition portion of the blade, three-dimensionally. In this illustration, some of the blade is cut off for clarity of illustration.

In embodiments of the invention, and referring now to FIG. 1A-2F, there may be provided a blade 10. The blade 10 may comprise, in sequence, a cutting portion 100, a transition portion 200, and a gripping portion 300. Blade 10 may have a longitudinal axis 15. Longitudinal axis 15 may extend along blade 10 in the direction from cutting portion 100 to transition portion 200 to gripping portion 300.

The cutting portion 100 may be planar or substantially planar. The cutting portion may have a flat surface extending from one lateral side to another opposed lateral side. Cutting portion 100 is illustrated as having a thickness "t," measured perpendicular to the flat surface, such that the thickness "t" is smaller than other dimensions of cutting portion 100. At whatever edge or edges are desired, the cutting portion 100 may have an edge that is suitable to cut a material. Any cutting edge may be sharp, or may be serrated, or may have a combination of these features or still other features. As illustrated, the tip or distal end of cutting portion 100 has a sharp edge 110. As illustrated, the two side edges of cutting portion 100 are not sharp, although they could be sharp if desired. Cutting portion 100 is illustrated as being substantially rectangular. However, other shapes could also be used if desired.

With particular reference now to FIGS. 1C and 2A-2F, gripping portion 300 may have a geometry that is non-planar. Gripping portion 300 may have a cross-sectional shape, in a cross-section taken in a sectioning plane that is perpendicular to longitudinal axis 15. As illustrated, gripping portion 300 has a cross-sectional shape that is generally V-shaped, but with the vertex of the V being less than fully sharp. In FIG. 1, the vertex is shown as being a rounded vertex. Of course, the vertex could if desired be sharp. Gripping portion 300 may have a concave surface 310 and a convex surface 320, opposed to concave surface 310.

In the illustrations herein, the cross-sectional shape of the gripping portion 300 is V-shaped with a vertex that is somewhat rounded rather than sharp. However, it is to be understood that other shapes are also possible, while still being non-planar. For example, the cross-sectional shape of the gripping portion 300 could be curved, such as continuously curved in the shape of an arc, such as an arc of a circle. Still another possibility is that the cross-sectional shape of the gripping portion 300 could be undulating with multiple reversals of curvature, such as an S-shape or a corrugation. In any such event, clamping surfaces of the chuck, described elsewhere herein, could be provided that are complementary to the respective surfaces of the cross-sectional shape of the gripping portion 300.

In a side view of blade 10, as shown particularly in FIG. 2F, cutting portion 10 can have a thickness "t" in what may be considered a vertical dimension. In the same vertical direction, gripping portion 300 may have a vertical direction (top extreme to bottom extreme) that is greater than thickness "t." Gripping portion 300 may have an upper extreme bounding plane that is parallel to the longitudinal axis 15 and just touches an extreme uppermost feature of gripping portion 300. Similarly, gripping portion 300 may have a lower extreme bounding plane that is parallel to the longitudinal axis 15 and just touches an extreme lowest feature of gripping portion 300.

As best illustrated in FIG. 2F, in an embodiment of the invention, the cutting portion 100 may be disposed midway between the upper extreme bounding plane of gripping portion 300 and the lower extreme bounding plane of gripping portion 300. More generally, the cutting portion 100 may be disposed anywhere between the upper extreme bounding plane of gripping portion 300 and the lower extreme bounding plane of gripping portion 300. However, even this relation is not essential. The vertical placement of cutting portion 100 could have any desired relation to the vertical placement of gripping portion 300. In fact, if desired, it is even possible that the cutting portion 100 could be outside of the range that is defined by the upper extreme bounding plane of the gripping portion 300 and the lower extreme bounding plane of the gripping portion 300, even if the cutting portion 100 and the gripping portion both extend generally along a common longitudinal axis 15.

Also shown in gripping portion 300 is a pair of recesses 320, one on each side of the "V" shape. These recesses 320 may interact with other components described elsewhere herein.

Also shown in FIGS. 1A and 2A-2F are blade tabs 340. Blade tabs 340 may extend in an appropriate configuration so as to limit the motion of a splash guard in a particular direction along the longitudinal axis 15 or to retain splash a guard in position. Blade tabs 340 may be formed by cutting and bending a piece of material from a remaining material of blade 10. There may be a blade tab 340 on each side of blade 10.

The transition portion 200 is especially illustrated in FIGS. 2A-2F and FIG. 3. In the transition portion 200 that is nearest cutting portion 100, the transition portion 200 can be nearly flat. In the transition portion 200 that is nearest gripping portion 300, the transition portion can have almost the same cross-section as gripping portion 300. In between, there can be transition surfaces that are smoothly curving surfaces appropriate to achieving the desired geometric transition.

FIG. 3 is a series of cross-sections of transition portion 200, taken sequentially from one end of transition portion 200 to the other end of transition portion 200. Again, this is for the situation where the gripping portion 300 has a cross-sectional shape that is generally V-shaped, with a slightly rounded vertex, and the cutting portion 100 is planar. These sections are viewed from a perspective upward from the blade 10. FIG. 3A shows blade 10 for purposes of labeling the cross-sections. FIG. 3B shows the cross-section that is taken closest to the gripping portion 300, and FIG. 3H shows the cross-section that is taken closest to the cutting portion 100. It can be seen that in FIG. 3B the cross-sectional shape has a V shape with a particular included angle of the vertex, and progressively this included angle becomes flatter and flatter until in FIG. 3H, corresponding to a point near the cutting portion 100, the included angle of the cross-sectional "V" shape is substantially equal to 180 degrees. Also shown in FIGS. 3B-3H is a series of sharp-vertexed "V" shapes that each correspond to the upper edge or lower edge of each cross-sectional shape. It can be seen that the included angle of the sharp-vertexed "V" becomes progressively shallower and shallower in this sequence. FIG. 3I is a compilation of those "V" shapes from FIGS. 3B-3H.

The lateral dimension of cutting portion 100 and the lateral dimension of gripping portion 300 can differ from each other, if desired, as is best illustrated in FIG. 2E. As illustrated, gripping portion 300 is wider than cutting portion 100. Accordingly, the edge of transition portion 200 can also be curved. For example, when blade 10 is viewed from above as in FIG. 2E, transition portion 200 has a curved smoothly transitioning width going from the width of cutting portion 100 to the width of gripping portion 300.

It can be appreciated that if there were an abrupt situation of a less-stiff cutting region 100 directly joining a gripping portion 300 having a substantially greater stiffness or a rigid fixation in a chuck, there would be a likelihood of experiencing a stress concentration factor. Thus, there could be an especially large stress near where the cutting region 100 joined the gripping region 300. It can be appreciated that the use of transition region 200 creates a situation where there is less of a stress concentration factor than in the abrupt situation.

The blade 10 can be symmetric around axis 15 in a side-to-side (lateral) direction.

In embodiments of the invention, it is possible that the cutting portion 100 can have a cutting portion thickness, and the gripping portion 300 can have a gripping portion thickness, and the cutting portion thickness can equal the gripping portion thickness. The transition portion 200 can also have the same thickness. In practical terms, this can correspond to the entire blade being formed from a single initial piece of material that could be sheet metal having a uniform thickness. However, alternatively, if desired, the thickness could vary from one place to another within the blade 10.

Figure 4A:
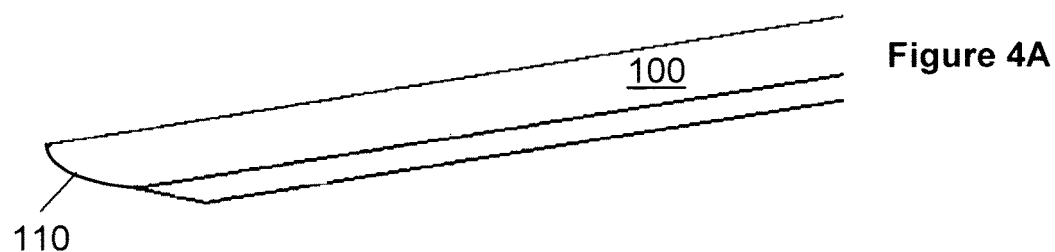
FIG. 4A shows a cutting edge that is convexly curved.
Figure 4B:
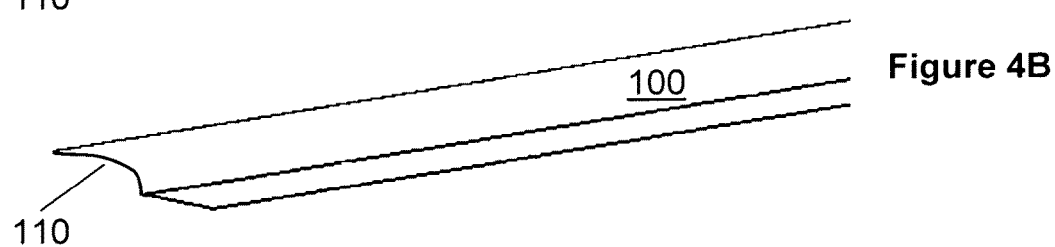
FIG. 4B shows a cutting edge that is concavely curved.

Referring now to FIGS. 4A-4B, it is illustrated that the front (cutting) edge 110 of cutting portion 100 does not have to be straight as has been illustrated in FIGS. 1A, 2E. Rather, the front (cutting) edge could be curved. A convexly curved cutting edge 110 is shown in FIG. 4A. A concavely curved is shown in FIG. 4B.

Figure 5A:
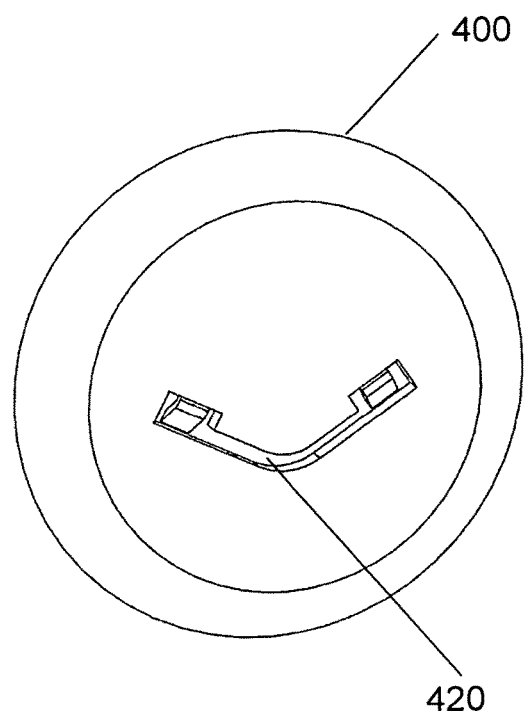
FIG. 5A is a front view of the splash guard.
Figure 5B:
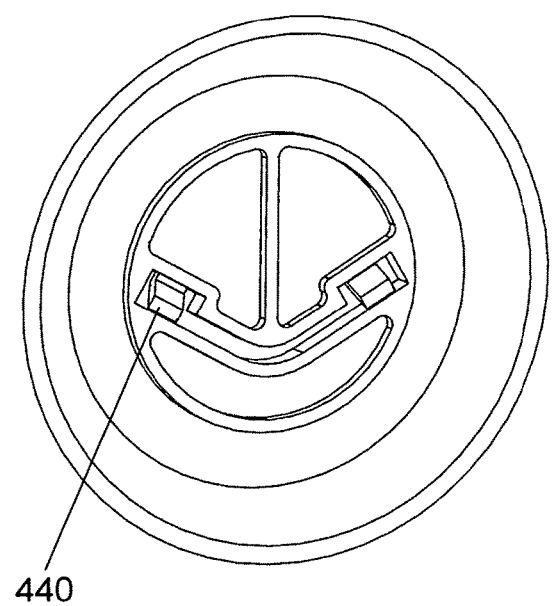
FIG. 5B is a rear view of the splash guard.

Referring now to FIGS. 5A-5B and also FIG. 1A, there is shown a splash guard 400 that is disposed on the gripping portion 300 of blade 10. Splash guard 400 may have an opening 420 therethrough that is similar in shape to the cross-sectional shape of gripping portion 300. It is possible that opening 420 can have some clearance with respect to gripping portion 300. Alternatively, and depending on the material of which splash guard 400 is made, splash guard 400 may be snugly fitting with respect to gripping portion 300. Splash guard 400 may also comprise a pair of splash guard tabs 440 that can interact with blade tabs 340 to retain splash guard 400 on blade 10.

Reference is now made to FIGS. 6A-11B, which illustrate a chuck 600 that is capable of gripping the blade 10. The chuck could be part of a larger tool, which could be any of a pneumatically powered tool, an electrically powered tool, or a hand-held tool, or generally any kind of tool or instrument. For example, the tool could be as described in co-pending U.S. patent application Ser. No. 14/848,228.

Figure 6C:
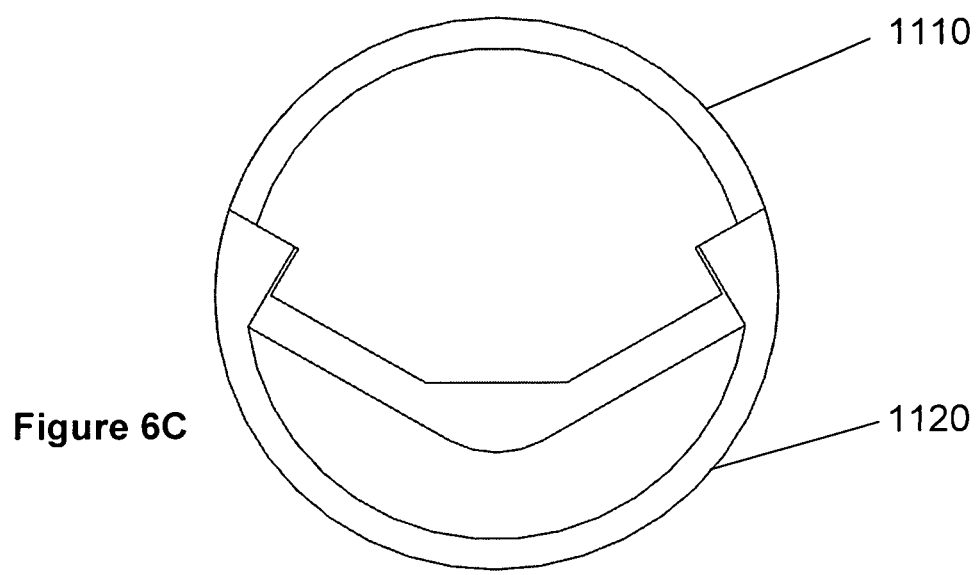
FIG. 6C is an end view showing the upper nest and the lower nest assembled to each other.

The gripping action of chuck 600 onto blade 10 may be provided by any one or more of various elements that can urge or bear against respective surfaces of the gripping portion 300, or simply constrain the location of gripping portion 300 within a desired close range. In FIGS. 5A-5C, it is shown that chuck 600 comprises an upper nest 1110 and a lower nest 1120. Upper nest 1110 may be complementary in shape with concave surface 310 of the gripping portion 300. Lower nest 1120 may be complementary in shape with convex surface 320 of the gripping portion 300. First of all, the shapes of gripping portion 300, upper nest 1110 and lower nest 1120 may be such that gripping portion 300 can slide into and out of the space between upper nest 1110 and lower nest 1120 along the direction of longitudinal axis 15. In combination, upper nest 1110 and lower nest 1120 may clamp onto gripping portion 300. This clamping action may allow force to be transmitted from blade 10 through the clamp action of upper nest 1110 and lower nest 1120, and thence to the rest of the blade holder. Alternatively, upper nest 1110 and lower nest 1120 may merely be close-fitting with respect to blade 10, and other components or means may be provided for capturing, trapping, restraining or clamping gripping portion 300 of blade 10. It is possible that the upper nest 1110 and the lower nest 1120 can fit within each other such that there is a trapping of the upper nest 1110 by the lower nest 1120, and the two components can only be assembled to each other by being slid relative to one another along the longitudinal axis 15. As is best illustrated in FIGS. 6B-6C, upper nest 1110 can have therein an angled slot 1112. Lower nest 1120 can have therein an angled slot 1122. Slots 1112 and 1122 can be located such that when upper nest 1110 and lower nest 1120 are assembled to each other, slots 1112 and 1122 are continuous with each other.

Figure 7A:
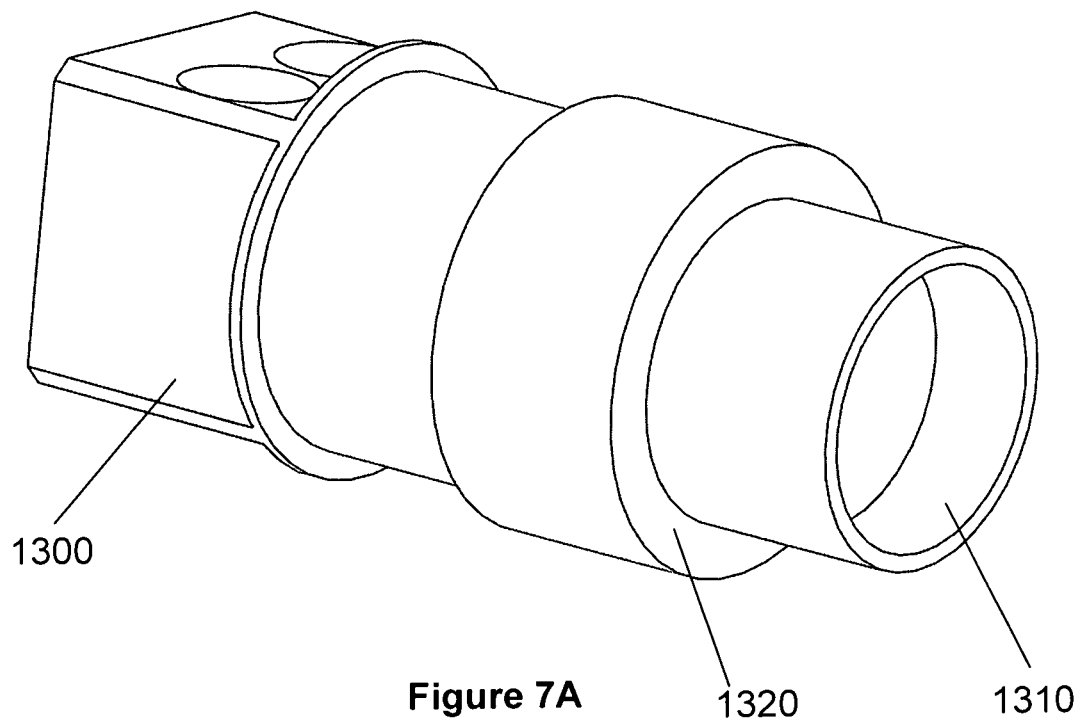
FIG. 7A is a three-dimensional perspective view of the base.
Figure 7B:
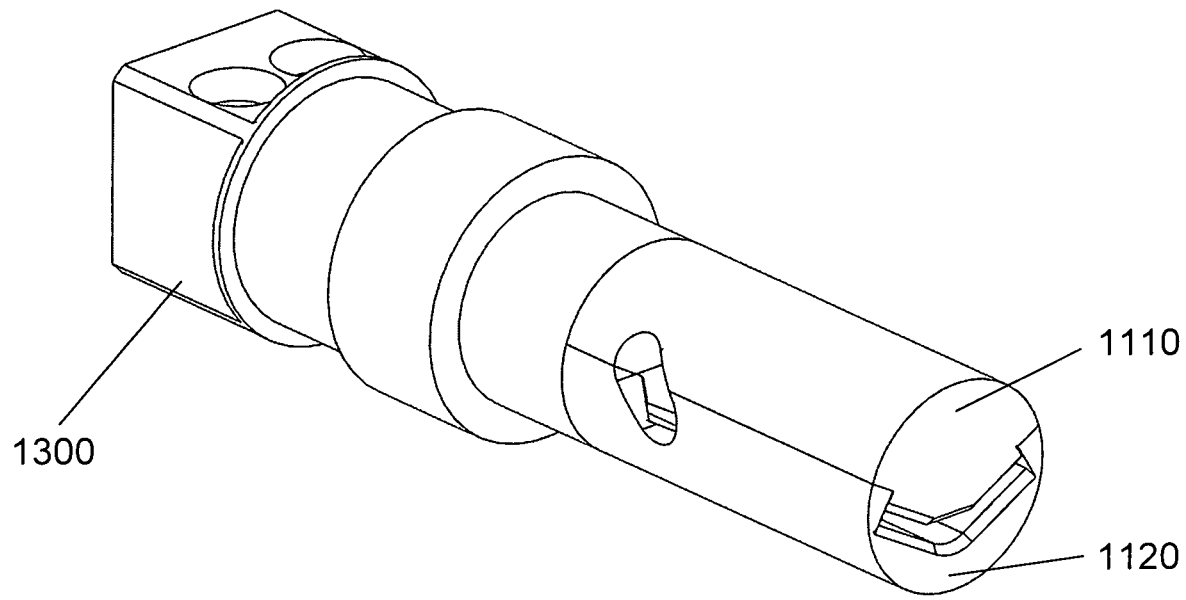
FIG. 7B is a three-dimensional perspective view of the base assembled together with the upper nest and the lower nest.
Figure 7C:
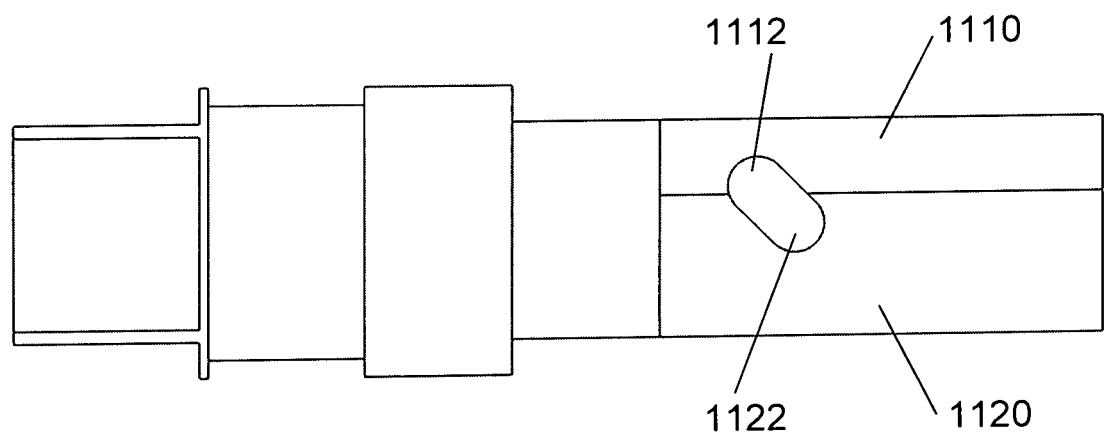
FIG. 7C is a view of the same assembly as FIG. 7B, but viewed purely from the side, making the slot more clearly visible.

FIG. 7A illustrates base 1300. Base 1300 may at its distal end have a circular recess 1310 that receives both upper nest 1110 and lower nest 1120. The ends of upper nest 1110 and lower nest 1120 that are received in the circular recess 1310 of base 1300 may together make substantially a fully cylindrical combination that is received in the circular recess 1310. The ends of upper nest 1110 and lower nest 1120 that are received in circular recess 1310 may be retained in circular recess 1310 by any suitable type of joining, including press-fit, welding, brazing, adhesive, or other known joining or combination thereof. There can also be provided a retaining ring 1380 (FIG. 11), which may be located at the distal ends of upper nest 1110 and lower nest 1120. Retaining ring 1380 may help to maintain the distal ends of upper nest 1110 and lower nest 1120 in contact with each other. FIG. 7B shows, from a perspective view, the assembly of the circular recess 1310, the upper nest 1110 and the lower nest 1120. FIG. 7C also shows this assembly, but from a side view. In FIG. 7C there can be seen slots 1112 and 1122.

Figure 8:
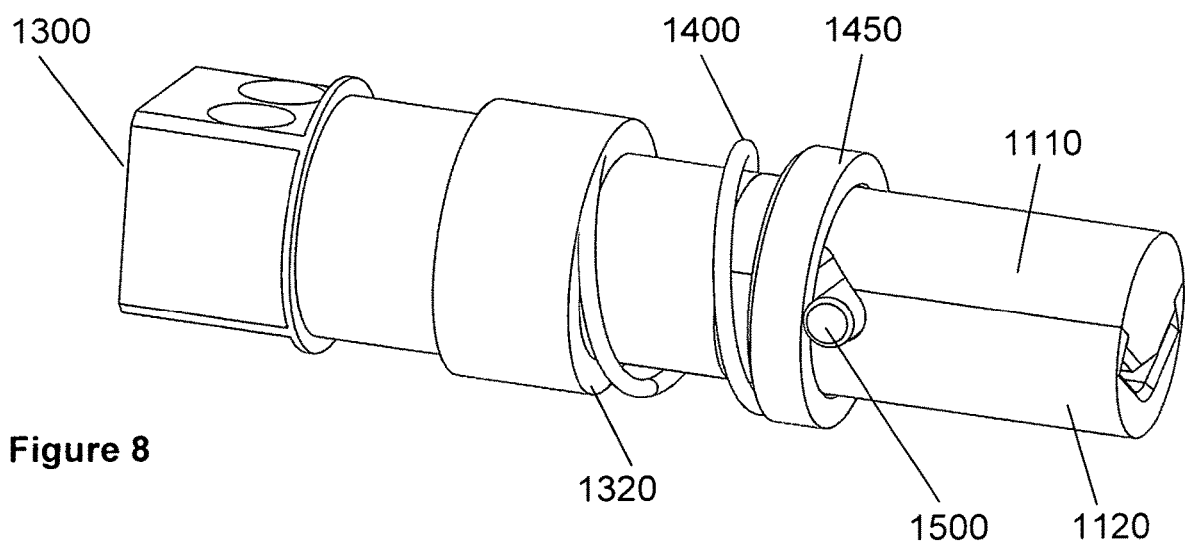
FIG. 8 shows an assembly of a base, an upper nest, a lower nest, a spring, a pressure ring and a pin.

Referring now to FIG. 8, there are shown the same components as in FIGS. 6B and 6C, but with the addition of spring 1400 and pressure ring 1450 and pin 1500. Pin 1500 may have dimensions that are appropriate for pin 1500 to fit within and slide in the path defined by slots 1112 and 1122. Spring 1400 may be such that spring 1400 reacts in a backward direction against a surface or ridge of base 1300, and reacts in a forward direction against pressure ring 1450. Pressure ring 1450 in turn may press against pin 1500. Pin 1500 in turn may, in its forward-most position, press against an internal ridge 1820 of outer sleeve 1800.

Figure 9:
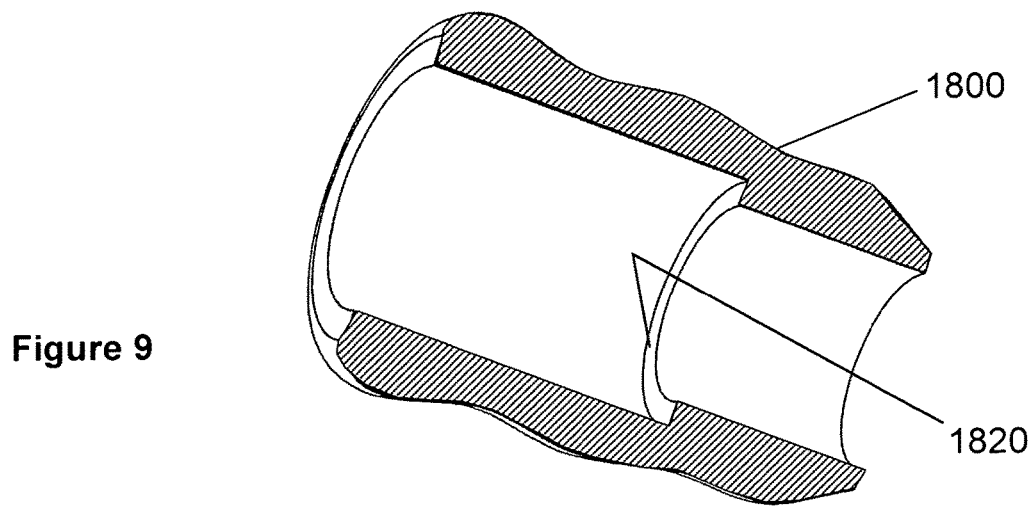
FIG. 9 shows an outer sleeve, sectioned by a plane that contains the longitudinal axis of the blade.
Figure 10:
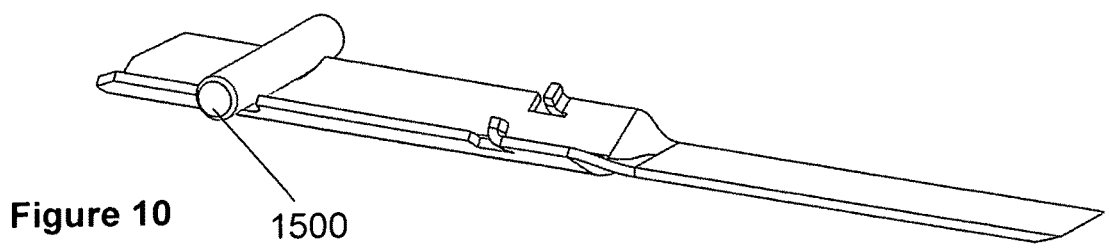
FIG. 10 shows a blade and a pin disposed relative to the blade.
Figure 11A:
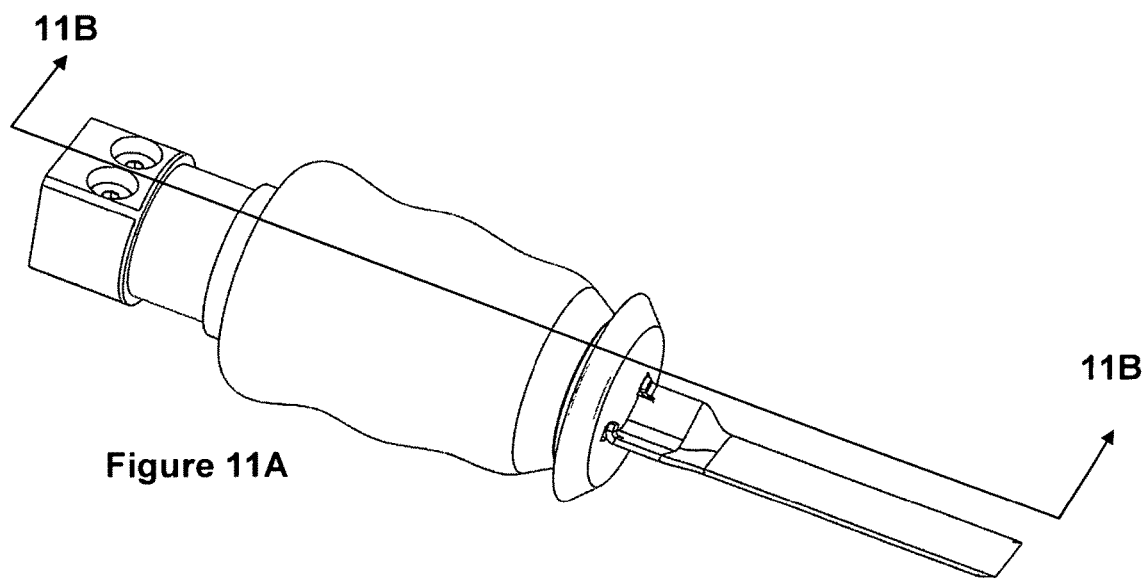
FIG. 11A is a three-dimensional perspective view of a chuck assembly.
Figure 11B:
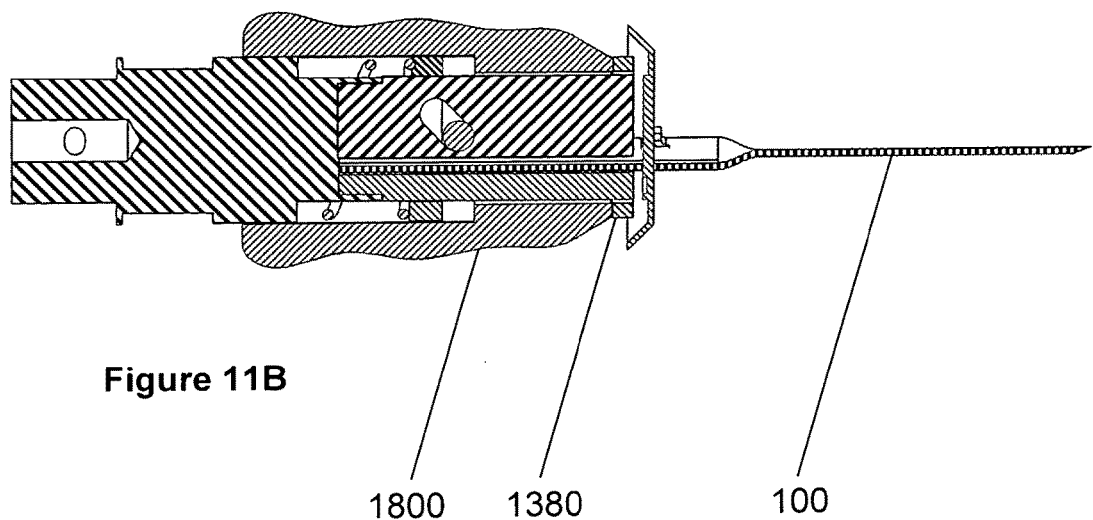
FIG. 11B shows a cross-section of the chuck assembly.

As illustrated in FIG. 9 and FIGS. 11A-11B, outer sleeve 1800 may generally surround upper nest 1110 and lower nest 1120. Outer sleeve may extend around the full circumference of the exterior of the chuck 600. Outer sleeve 1800 may be axisymmetric with respect to longitudinal axis 15. In FIG. 9, outer sleeve is shown sectioned by a plane that contains longitudinal axis 15. On its interior, outer sleeve 1800 may have a ridge 1820, which may extend around the full internal circumference of outer sleeve 1800.

Within outer sleeve 1800, there may be provided a spring 1400 that urges pressure ring 1450 and pin 1500 in a forward or distal direction. In order to disengage a blade 10 from the chuck 600 or install a blade 10 into the chuck 600, the required action may be to pull the outer sleeve 1800 in a proximal or backward direction. One end of spring 1400 may react against pressure ring 1450. Pressure ring 1450 may in turn press against pin 1500. Another end of spring 1400 may react against ridge 1320 on base component 1300. Pin 1500 may in turn bear against the internal ridge 1820 of outer sleeve 1800.

Outer sleeve 1800 may be suitable to be grasped on its exterior surface by a user who wishes to release a blade 10 from the chuck 600 or to open the chuck 600 to accept a blade 10. Pulling outer sleeve 1800 in a backward (distal) direction may cause pin 1500 to similarly move backward (distally), which may compress spring 1400. At the same time, causing pin 1500 to move backward (distally) causes pin 1500 to slide along the ramp created by slots 1112, 1122, with the result that the pin 1500 is displaced away from the longitudinal axis 15. This away-from-axis motion displaces the pin 1500 out of the recesses 320 in the blade 10, thereby allowing the blade 10 (if present) to be released from chuck 600. If no blade 10 is present in the chuck 600, such motion will allow a blade 10 to be inserted into chuck 600. If the outer sleeve 1800 is retracted, allowing the outer sleeve 1800 to return forward (distally) will cause pin 1500 to slide along the ramp created by slots 1112, 1122 in a direction that moves the pin 1500 toward the longitudinal axis 15 and captures a blade 10 within chuck 600.

In an overall view of embodiments of the invention and their potential advantages, it can be useful to consider bending stiffness of a blade such as blade 10. Such bending stiffness can refer to bending in the direction around an axis that lies in the lateral (side to side) direction of the cutting portion 100 of blade 10, as identified in FIG. 1A. It can be appreciated that, for a given thickness dimension and other dimensions of cutting portion 100, and for given mechanical properties of the material of which cutting portion 100 is made, a planar blade such as cutting portion 100 has only a limited amount of bending stiffness. In contrast, a gripping portion 300 that is made out of the same material as cutting portion 100 is made, and has generally the same material thickness as cutting portion 100, but is non-planar, can be expected to have substantially greater bending stiffness than cutting portion 100. This advantage is obtained because gripping portion 300 has a more favorable distribution of material as described by the parameter moment of inertia, as is conventionally used in calculations of bending and stress. Similarly, the bending stiffness of transition portion 200 can be expected to be greater than that of cutting portion 100, although the bending stiffness of transition portion 200 might not be as large as that of gripping portion 300.

It can be appreciated that this increased stiffness can be of benefit in orthopedic surgery for the following reasons. It is typically desirable that the cutting portion 100 be as thin as possible in the direction of the labeled thickness "t," because such dimension determines the kerf dimension of removed material such as bone, and it may be desirable for the kerf dimension or the amount of removed material to be as small as possible. Also, minimizing the thickness of the cutting portion 100 of the blade 10 may contribute to minimizing the size of the incision, which is a generally beneficial goal. However, minimizing such thickness of cutting portion 100 does reduce bending stiffness in the indicated direction. Accordingly, at whatever location at which it is no longer necessary to minimize such thickness of the blade 10, it can be appropriate to introduce a geometric change in the blade configuration such as to increase the local stiffness of the blade. Such geometric change occurs at the transition portion 200 as disclosed herein. Then, the gripping portion 300 has a stiffness that is greater than the stiffness of cutting portion 100. The stiffness of gripping portion 300 may also be greater than the stiffness of transition portion 200. It is furthermore believed, although it is not wished to be limited to this explanation, that the gradually changing nature of transition portion 200 results in little or no stress concentration factor in the vicinity of the transition portion 200.

If chuck 600 is connected to a power tool such as an osteotome, the power tool may oscillate blade 10 in a forward-rearward (proximal-distal) direction. This would be consistent with the illustrated blade 10 having a sharp edge on its forward (distal) edge. However, in other embodiments, it is possible that a power tool could oscillate blade 10 in a side-to-side pattern of motion. In such a situation, other edges of the cutting portion could be sharp or shaped for purposes of cutting. Of course, still other patterns of motion and blade edge configuration are also possible.

In regard to materials, blade 10 may in general be made of a metal that is suitable for use in a surgical setting. Splash guard 400 may be made of a polymer such as rubber. Chuck 600 may generally be made of a suitable metal, although other materials are also possible.

In general, any combination of disclosed features, components and methods described herein is possible.

All cited references are incorporated by reference herein.

Although embodiments have been disclosed, it is not desired to be limited thereby. Rather, the scope should be determined only by the appended claims.

I claim:

1. A blade for use in cutting, said blade comprising:
   a cutting portion;
   a transition portion that is continuous with said cutting portion; and
   a gripping portion that is continuous with said transition portion,
   wherein said blade has a longitudinal axis,
   wherein said cutting portion is planar having a cutting portion planar surface facing in an upward direction and has at least one cutting edge that is adapted for cutting,
   wherein said gripping portion has an upward-facing surface facing generally in said upward direction and said upward-facing surface does not entirely lie in a single plane, and
   wherein said transition portion has a three-dimensional surface transitioning between said cutting portion and said gripping portion.

2. The blade of claim 1, wherein said gripping portion has a cross-sectional shape taken in a cross-sectional plane that is perpendicular to said longitudinal axis, wherein said cross-sectional shape is a "V" shape having either a pointed vertex or a rounded vertex.

3. The blade of claim 1, wherein said gripping portion has a cross-sectional shape taken in a cross-sectional plane that is perpendicular to said longitudinal axis, wherein said cross-sectional shape is a curved shape.

4. The blade of claim 1, wherein said at least one cutting edge has a sharp edge or has a serration.

5. The blade of claim 1, wherein said cutting portion has a cutting portion thickness and said gripping portion has a gripping portion thickness, said thicknesses being measured perpendicular to a local surface of said blade, and said cutting portion thickness equals said gripping portion thickness.

6. The blade of claim 1, wherein said three-dimensional surface connecting said cutting portion with said gripping portion is a smoothly curved surface.

7. The blade of claim 1, wherein said gripping portion is wider than said cutting portion.

8. The blade of claim 1, wherein an outer perimeter of said blade is smoothly contoured from said cutting portion to said gripping portion.

9. The blade of claim 1, wherein said gripping portion has an upper extreme bounding plane parallel to said longitudinal axis and has a lower extreme bounding plane parallel to said longitudinal axis, and wherein said cutting portion lies between said extreme bounding planes.

10. The blade of claim 1, wherein said gripping portion has an upper extreme bounding plane parallel to said longitudinal axis and has a lower extreme bounding plane parallel to said longitudinal axis, and wherein, with respect to a direction perpendicular to a primary flat surface of said cutting portion, said cutting portion is located midway between said upper extreme bounding plane and said lower extreme bounding plane.

11. The blade of claim 1, wherein said cutting portion has a cutting portion thickness and said transition portion has a vertical dimension, and a ratio of said vertical dimension to said cutting portion thickness is in a range of from 2:1 to 10:1.

12. The blade of claim 1, wherein said cutting portion has a cutting portion thickness and said transition portion has a proximal-distal dimension, and a ratio of said proximal-distal dimension to said cutting portion thickness is in a range of from 2:1 to 10:1.

13. The blade of claim 1, wherein said transition portion has a proximal-distal dimension and said transition portion has a vertical dimension, and a ratio of said vertical dimension to said cutting portion thickness is in a range of from 2:1 to 1:2.

14. The blade of claim 1, wherein said cutting edge of said cutting portion has a shape that is selected from the group consisting of straight, concavely curved, and convexly curved.

15. The blade of claim 1, further comprising a splash guard, wherein said splash guard has an opening through which said gripping portion fits.

16. An apparatus comprising the blade of claim 1, in combination with a chuck, wherein said chuck comprises an upper nest and a lower nest, wherein said upper nest is complementary to a first surface of said gripping portion of said blade, and said lower nest is complementary to a second surface, that is opposed to said first surface, of said gripping portion of said blade.

17. The apparatus of claim 16, wherein said gripping portion comprises a recess adjoining an edge of said gripping portion, and wherein said chuck further comprises a pin that is movable between a first pin position and a second pin position, wherein in said first pin position said pin engages with said recess in said gripping portion, and in said second pin position said pin does not engage with said recess in said gripping portion.

18. The apparatus of claim 17, further comprising an outer sleeve that is movable in a direction of said longitudinal axis, wherein motion of said outer sleeve causes motion of said pin, and further comprising a spring, wherein said spring urges said pin to said second pin position.

19. The blade of claim 1, wherein said blade has, passing through said longitudinal axis, a central plane of symmetry that is generally perpendicular to said cutting portion, and wherein said gripping portion comprises a first planar surface on a first side of said central plane of symmetry and comprises a second planar surface on a second side, opposite said first side, of said central plane of symmetry, said first planar surface and said second planar surface being not coplanar with each other.

20. The blade of claim 19, wherein said first planar surface and said second planar surface join each other at an edge.

\* \* \* \* \*